(12) United States Patent
Tanaami

(10) Patent No.: US 9,462,946 B2
(45) Date of Patent: Oct. 11, 2016

(54) OPHTHALMOLOGIC APPARATUS AND CONTROL METHOD FOR THE SAME

(71) Applicant: CANON KABUSHIKI KAISHA, Tokyo (JP)

(72) Inventor: Ryuji Tanaami, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/641,584

(22) Filed: Mar. 9, 2015

(65) Prior Publication Data

US 2015/0265149 A1 Sep. 24, 2015

(30) Foreign Application Priority Data

Mar. 19, 2014 (JP) ................................ 2014-056456

(51) Int. Cl.
| | |
|---|---|
| *A61B 3/10* | (2006.01) |
| *A61B 3/14* | (2006.01) |
| *A61B 3/00* | (2006.01) |
| *A61B 3/15* | (2006.01) |

(52) U.S. Cl.
CPC ................................... *A61B 3/152* (2013.01)

(58) Field of Classification Search
CPC ...... A61B 3/103; A61B 3/1015; A61B 3/12; A61B 3/14; A61B 3/152; A61B 3/113; A61B 3/1225; A61B 3/024; A61B 3/18

USPC ........ 351/200, 205, 206, 208–210, 221–222, 351/245–246
See application file for complete search history.

(56) References Cited

U.S. PATENT DOCUMENTS

| | | | |
|---|---|---|---|
| 2009/0079939 A1* | 3/2009 | Mimura | A61B 3/0033 351/245 |
| 2013/0162945 A1 | 6/2013 | Tanaami | |
| 2013/0293847 A1* | 11/2013 | Tanaami | A61B 3/0075 351/245 |

FOREIGN PATENT DOCUMENTS

JP 2003-220029 A 8/2003

* cited by examiner

*Primary Examiner* — Dawayne A Pinkney
(74) *Attorney, Agent, or Firm* — Fitzpatrick, Cella, Harper & Scinto

(57) ABSTRACT

As an ophthalmologic apparatus for reducing time required for driving an inspection unit during alignment of an eye to be inspected with the inspection unit, and at the same time, improving stopping accuracy of the inspection unit, the apparatus includes an eye inspection unit configured to inspect the eye to be inspected of a subject, a first drive unit configured to drive the eye inspection unit in a predetermined direction, a second drive unit arranged to be able to move the eye inspection unit in the predetermined direction, and a switching unit configured to switch drive between the first drive unit and the second drive unit.

17 Claims, 9 Drawing Sheets

OPHTHALMOLOGIC APPARATUS AND CONTROL METHOD FOR THE SAME

BACKGROUND OF THE INVENTION

1. Field of the Invention

The present invention relates to an ophthalmologic apparatus for performing alignment with respect to an eye to be inspected to perform an eye inspection or the like, and a control method for controlling the ophthalmologic apparatus.

2. Description of the Related Art

There has been widely known an ophthalmologic apparatus including, in order to reduce inspection time, a switching unit for detecting a working distance between an eye to be inspected and the apparatus, and switching a moving speed of the apparatus when a position of the apparatus with respect to the eye to be inspected becomes a predetermined distance or shorter. In Japanese Patent Application Laid-Open No. 2003-220029, there is disclosed a configuration in which the moving speed of the up and down drive unit is switched when the position of the apparatus with respect to the eye to be inspected becomes the predetermined distance or shorter.

The ophthalmologic apparatus disclosed in Japanese Patent Application Laid-Open No. 2003-220029 uses as a drive unit a moving mechanism that is generally called "rack and pinion". The moving mechanism is suitable for driving at a relatively high speed, and is used to reduce alignment time. Moreover, high-speed and low-speed driving modes are specified for the moving mechanism, and the driving modes are selectively used to satisfy the demand for the stopping accuracy. However, the moving mechanism is difficult to obtain a certain stopping accuracy or higher due to its structure, and there is a need for improvement in order to obtain the current high-definition image of the eye to be inspected.

SUMMARY OF THE INVENTION

The present invention has been made in view of the above-mentioned circumstances, and therefore has an object to provide an ophthalmologic apparatus, which is capable of reducing time required for alignment between an inspection unit and an eye to be inspected, and improving stopping accuracy of the inspection unit.

In order to solve the above-mentioned problem, according to one embodiment of the present invention, there is provided an ophthalmologic apparatus, including:

an eye inspection unit configured to inspect an eye to be inspected of a subject;

a first moving unit configured to move the eye inspection unit in a predetermined direction;

a second moving unit arranged to be able to move the eye inspection unit in the predetermined direction; and a switching unit configured to switch between the movement by the first moving unit and the movement by the second moving unit.

Further, in order to solve the above-mentioned problem, according to one embodiment of the present invention, there is provided a method of controlling an ophthalmologic apparatus, including:

moving an eye inspection unit configured to inspect an eye to be inspected of a subject along a predetermined direction toward the eye to be inspected by a first moving unit; and switching from the movement by the first moving unit to movement by a second moving unit to move the eye inspection unit along the predetermined direction.

With the ophthalmologic apparatus according to one embodiment of the present invention, in the case of performing the alignment between the eye to be inspected and the inspection unit, the moving speed of the inspection unit is suitably switched to attain the reduction in inspection time and the improvement in stopping accuracy.

Further features of the present invention will become apparent from the following description of exemplary embodiments with reference to the attached drawings.

DESCRIPTION OF THE EMBODIMENTS

Preferred embodiments of the present invention will now be described in detail in accordance with the accompanying drawings.

[First Embodiment]

(Configuration of Ophthalmologic Apparatus)

Figure 1A:
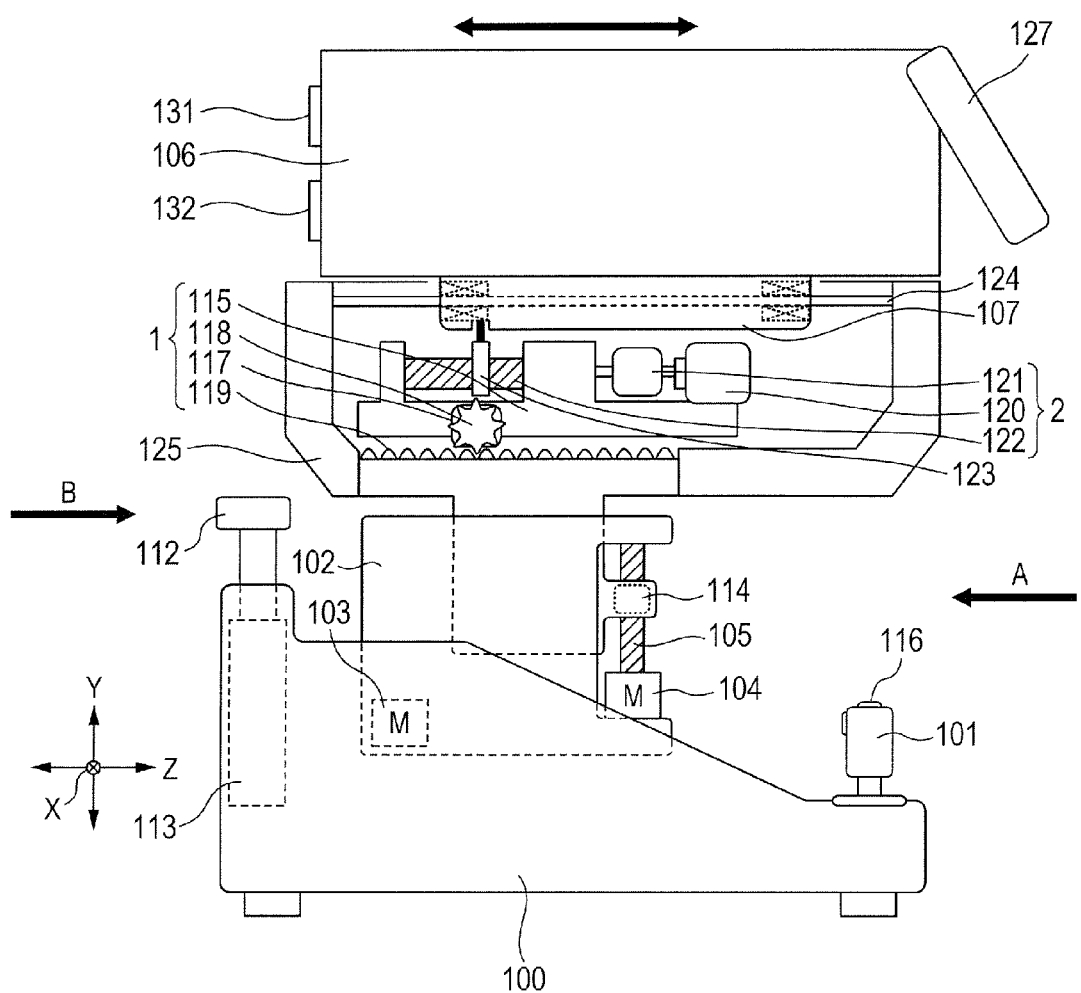
FIG. 1A is an overall view illustrating an ophthalmologic apparatus according to a first embodiment of the present invention.

An overall structure of an ophthalmologic apparatus according to a first embodiment of the present invention is described with reference to FIG. 1A. FIG. 1A is a side view schematically illustrating a configuration of the ophthalmologic apparatus according to this embodiment. The arrow A in FIG. 1A indicates a side on which an inspector (operator) who conducts an eye inspection is located and a direction in which the inspector is facing, and the arrow B indicates a side on which a subject who receives the eye inspection is located and a direction in which the subject is facing.

The ophthalmologic apparatus includes a fixed stage (base) 100, an X movable stage 102, a Y movable stage 125, a Z movable stage 107, drive (moving) mechanisms for driving or moving the movable stages, respectively, and an inspection unit 106 as an eye inspection unit. The inspection unit 106 includes, as the eye inspection unit, a tonometry unit (not shown) for measuring an ocular tension, and a diopter measuring unit (not shown) for measuring eye refractive power. The tonometry unit includes a tonometry beam radiation portion 131, and the diopter measuring unit includes a diopter measuring beam radiation portion 132. Note that, in this embodiment, the tonometry unit and the diopter measuring unit are used for description, but an eye axial length measuring unit and other such measurement units may be used instead.

The inspection unit 106 includes a monitor 127 as an indicating unit. Then, the monitor 127 may display an image of an imaged eye to be inspected, a menu for operating or setting the inspection unit 106, and other predetermined information.

The fixed stage 100 includes a chin rest part 112, a chin rest drive unit 113 for driving the chin rest part 112, and a joystick 101. The chin rest part 112 is a support on which the chin of the subject is put during the eye inspection. The chin rest part 112 is movable in an up and down direction (Y axis direction) with respect to the fixed stage 100 by a driving force provided by the chin rest drive unit 113. The joystick 101 is an operation member used to operate the X movable stage 102, the Y movable stage 125, and the Z movable stage 107. The joystick 101 includes a button (inspection switch, see FIG. 1B) 116.

The X movable stage 102 has a configuration that is movable in a left and right direction (this direction is referred to as "X axis direction") with respect to the fixed stage 100 when viewed from the subject who receives the eye inspection. The fixed stage 100 includes an X movable stage drive unit 96 (see FIG. 1B), and the X movable stage 102 moves in the X axis direction by a driving force generated by the X movable stage drive unit 96. A detailed description thereof is provided later.

The Y movable stage 125 includes a Y movable stage drive unit 97 (see FIG. 1B) that is movable in the up and down direction (this direction is referred to as "Y axis direction") with respect to the fixed stage 100 when viewed from the subject who receives the eye inspection. The Y movable stage drive unit 97 is arranged between the Y movable stage 125 and the X movable stage 102 to be driven by a motor 104 as a driving force generation unit and support the Y movable stage 125. Then, the Y movable stage 125 moves in the Y axis direction by a driving force of the motor 104.

Figure 1B:
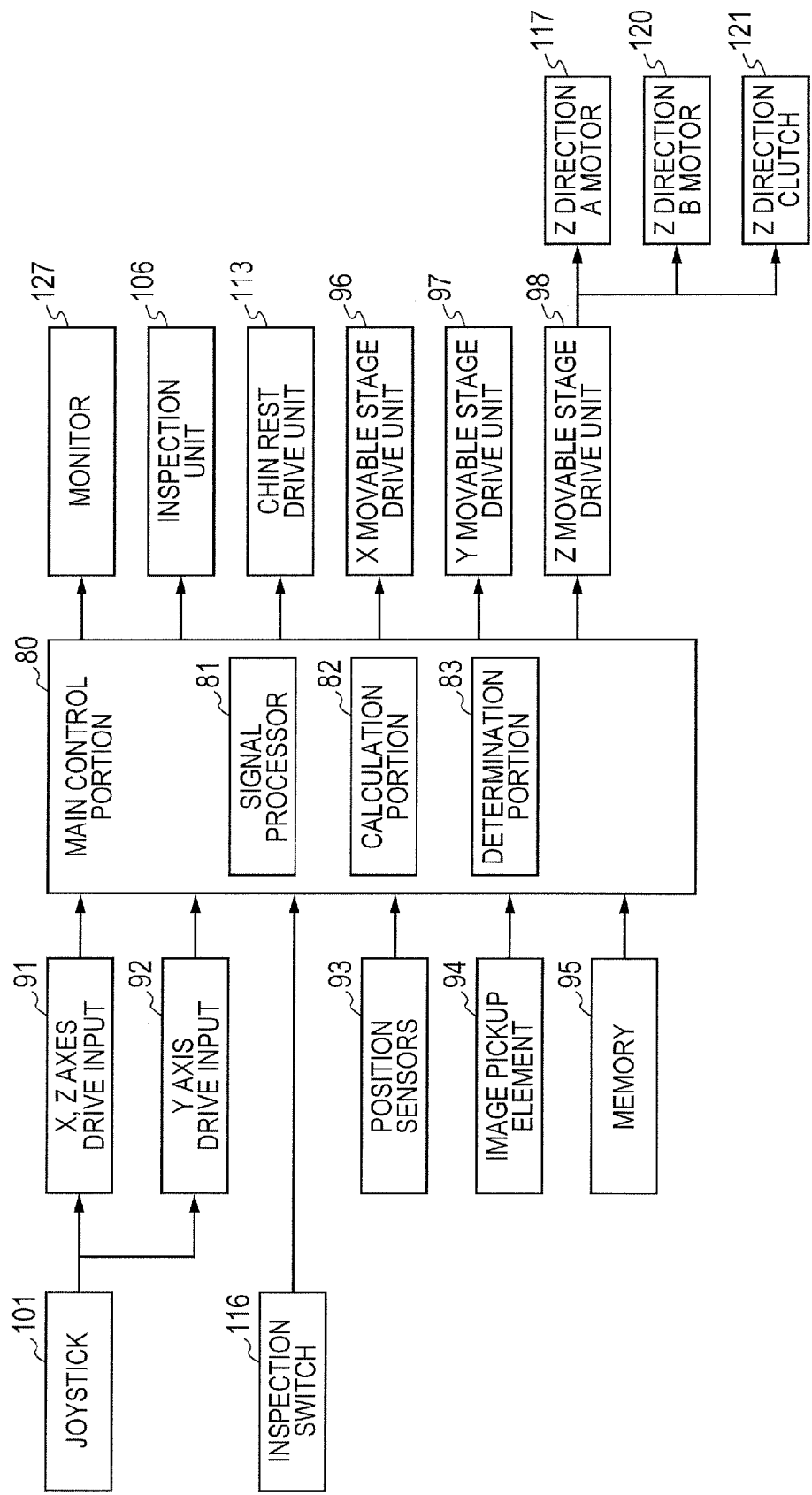
FIG. 1B is a block diagram illustrating functional components of the ophthalmologic apparatus.

Next, functional components of the ophthalmologic apparatus according to this embodiment are described with reference to a block diagram of FIG. 1B. The ophthalmologic apparatus is controlled by a main control portion 80. The main control portion 80 receives an XZ axes drive input 91 and a Y axis drive input 92 from the joystick 101, inputs on a start of the inspection and the like from the inspection switch 116, inputs on positions and the like of the movable stages from position sensors 93, and inputs from an image pickup element 94 for obtaining an image signal of the eye to be inspected and from a memory 95. The main control portion 80 includes a signal processor 81, a calculation portion 82, and a determination portion 83. The signal processor 81 executes generation of an eye-to-be-inspected image and the like by, for example, processing the image signal input by the image pickup element 94. The calculation portion 82 performs calculation of a position of the inspection unit 106 with respect to the eye to be inspected based on the inputs from the position sensors 93 and the like. The determination portion 83 executes a determination on whether or not it is necessary to switch among a plurality of driving motors, which are to be described later, based on the position calculated by the calculation portion 82 and a threshold value stored in advance in the memory 95, and the like.

The main control portion 80 outputs, to the monitor 127, the inspection unit 106, the chin rest drive unit 113, the X movable stage drive unit 96, the Y movable stage drive unit 97, and a Z movable stage drive unit 98, instructions on operations thereof. In this embodiment, a Z direction A motor 117, a Z direction B motor 120, and a Z direction clutch 121, which are to be described later, are included as the Z movable stage drive unit 98, and control signals are output thereto.

Figure 2:
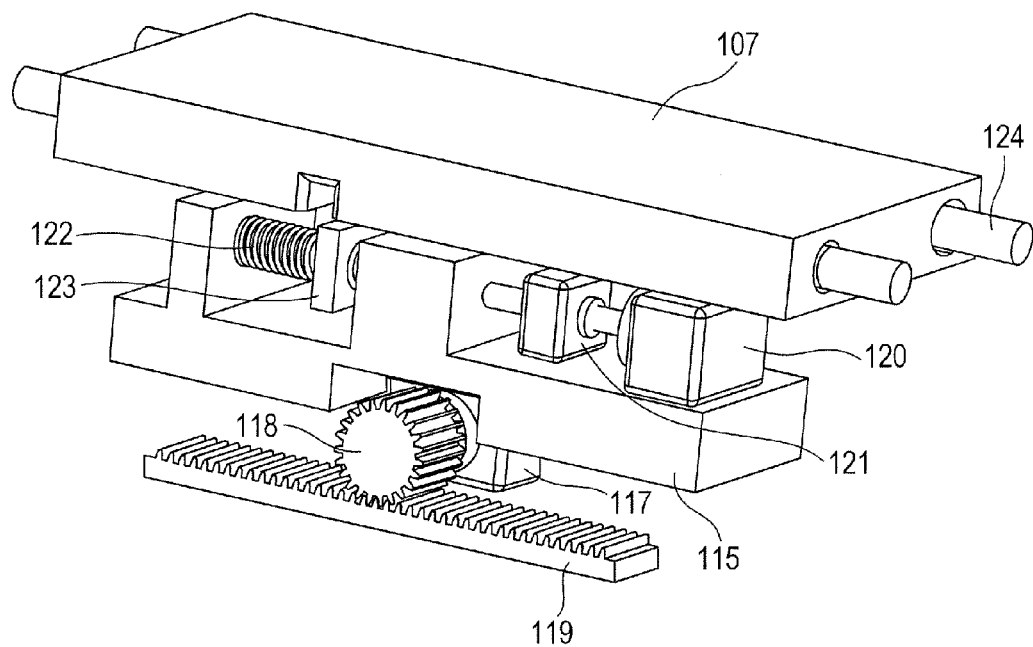
FIG. 2 is a view illustrating an overall structure of a Z direction moving mechanism in the ophthalmologic apparatus illustrated in FIG. 1A.

Next, the Z movable stage 107 and the Z movable stage drive unit 98 for moving the Z movable stage are described with reference to FIGS. 1A and 2.

The Z movable stage 107 as a movable unit in this embodiment has a configuration that is movable in a front and back direction (this direction is referred to as "Z axis direction") with respect to the fixed stage 100 when viewed from the subject who receives the eye inspection. A Z movable substage 115 is provided below the Z movable stage 107, and forms a first Z direction moving mechanism 1 as a first drive unit together with a motor and a pinion, which are to be described later. On the Z movable substage 115, a second Z direction moving mechanism 2 as a second drive unit is arranged. The first and second drive units drive the inspection unit 106 in the same predetermined direction, which is the Z axis direction herein. The Z movable stage 107 supports the inspection unit 106, and includes a guide member 124 held in a holding portion of the Y movable stage 125 to receive a load of the inspection unit 106. The guide member 124 supports the Z movable stage 107 to be slidable in the Z axis direction with respect to the Y movable stage 125.

Figure 3:
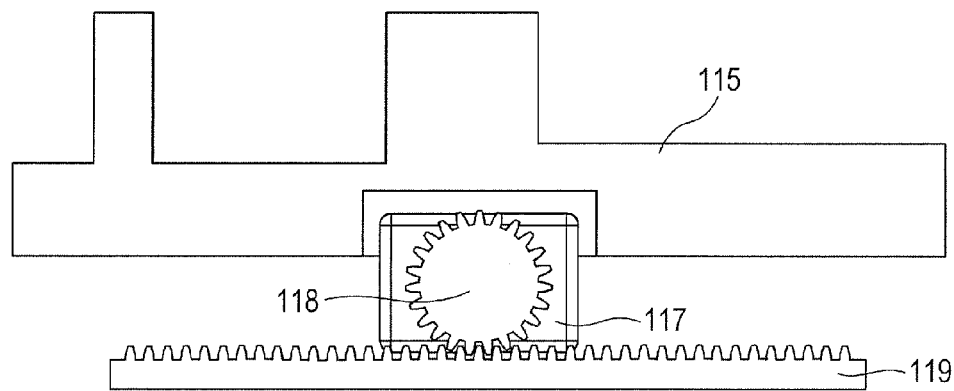
FIG. 3 is a view illustrating a first Z direction moving mechanism in the Z direction moving mechanism illustrated in FIG. 2.

Next, referring to FIG. 3, a configuration of the first Z direction moving mechanism 1 is described. The first Z direction moving mechanism 1 includes the Z movable substage 115, the Z direction A motor 117, a Z direction pinion 118, and a Z direction rack 119, which is arranged on the Y movable stage 125. The Z direction A motor 117 is arranged in the Z movable substage 115. Rotation of the Z direction A motor 117 is transmitted to the Z direction pinion 118 via a drive transmission unit (not shown) such as a gear. The Z direction pinion 118 is engaged with the Z direction rack 119, and hence a driving force generated by the Z direction A motor is converted into a driving force for moving the Z movable substage 115.

Figure 4:
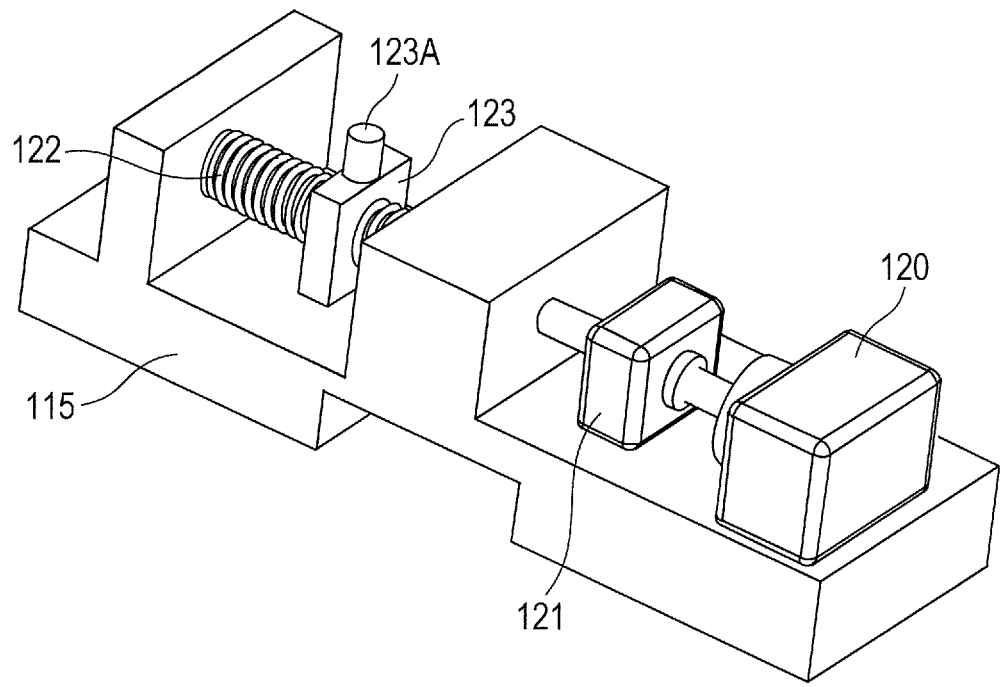
FIG. 4 is a view illustrating a second Z direction moving mechanism in the Z direction moving mechanism illustrated in FIG. 2.

Next, referring to FIG. 4, a configuration of the second Z direction moving mechanism 2 is described. The second Z direction moving mechanism 2 is provided on the Z movable substage 115, and includes the Z direction B motor 120, the Z direction clutch 121 as a switching unit, and a Z direction feed screw 122. The Z direction feed screw 122 is provided with a Z direction nut 123. Moreover, the Z direction feed screw 122 is held by a holding portion provided in the Z movable substage 115. The Z direction clutch 121 provided between the Z direction B motor 120 and the Z direction feed screw 122 transmits rotation of the Z direction B motor 120 to the Z direction feed screw 122 in response to an actuation signal from the main control portion (not shown).

An electromagnetic clutch and a mechanical clutch are generally known as the clutch, but another system may be used as long as the mechanism transmits and interrupts the drive.

Figure 5:
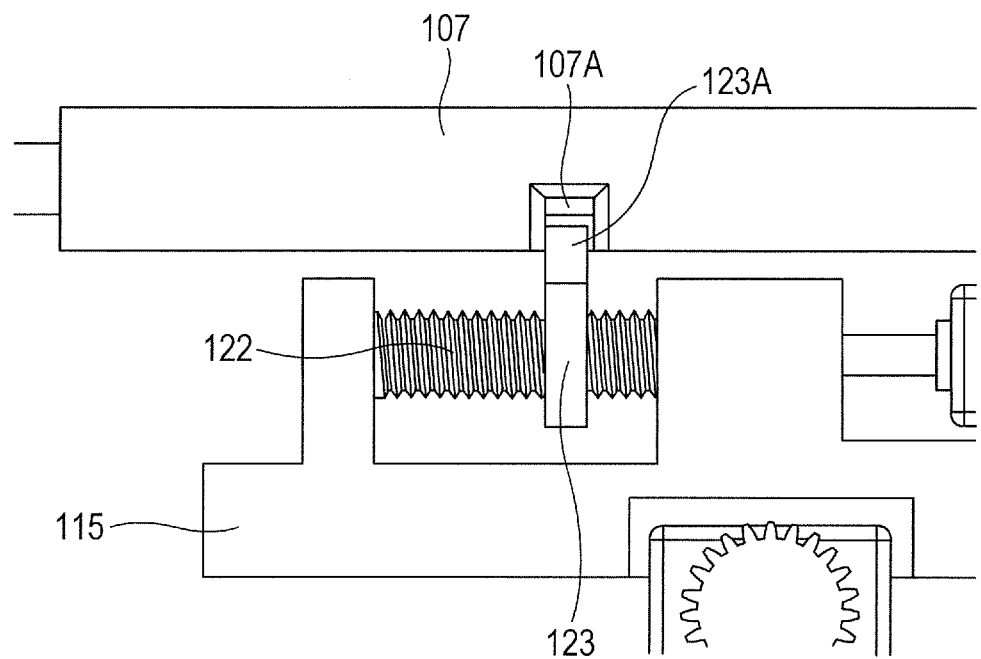
FIG. 5 is a view illustrating a state in which a protruding portion of a nut and a groove portion of a Z movable stage are engaged with each other.

When the Z direction B motor 120 is rotatably driven to rotate the Z direction feed screw 122, the Z direction nut 123 moves in the Z direction depending on a rotational number and a rotation direction of the Z direction feed screw 122. On the upside of the Z direction nut 123, a protruding shape portion 123A is provided as illustrated in FIG. 4. The protruding shape portion 123A and a groove portion 107A of the Z movable stage 107, which is arranged above the Z direction nut 123, are engaged with each other (see FIG. 5). Therefore, when the Z direction nut 123 moves on the Z direction feed screw 122 in the Z direction, the Z movable stage 107 also moves in the Z direction.

As described above, in this embodiment, the first Z direction moving mechanism 1 as the first drive (moving) unit, which uses a rack and pinion, and the second Z direction moving mechanism 2 as the second drive (moving) unit, which is provided in the first Z direction moving mechanism 1 and uses the Z direction feed screw 122, are provided as the drive units. More specifically, the first drive unit and the second drive unit are different in stopping accuracy, and the second drive unit has a higher stopping accuracy in this example. The drive units, and further the switching unit (not shown) for switching between the drive units in response to a signal from the main control portion are provided to enable one of the drive units to be driven. Moreover, the switching unit may be utilized to drive both the drive units at the same time.

Further, the first drive unit described above is moved by the driving force from the Z direction A motor 117 as a first motor being transmitted by a first transmission, which is a function of the rack and pinion or the like. Similarly, the second drive unit is also moved by a driving force from the Z direction B motor 120 as a second motor being transmitted by a second transmission, which is a function of the clutch and the feed screw or the like. The switching unit including the clutch or the like may also be understood to switch a used transmission method between the first transmission and the second transmission.

(Flow of Switching the Drive)

Figure 7:
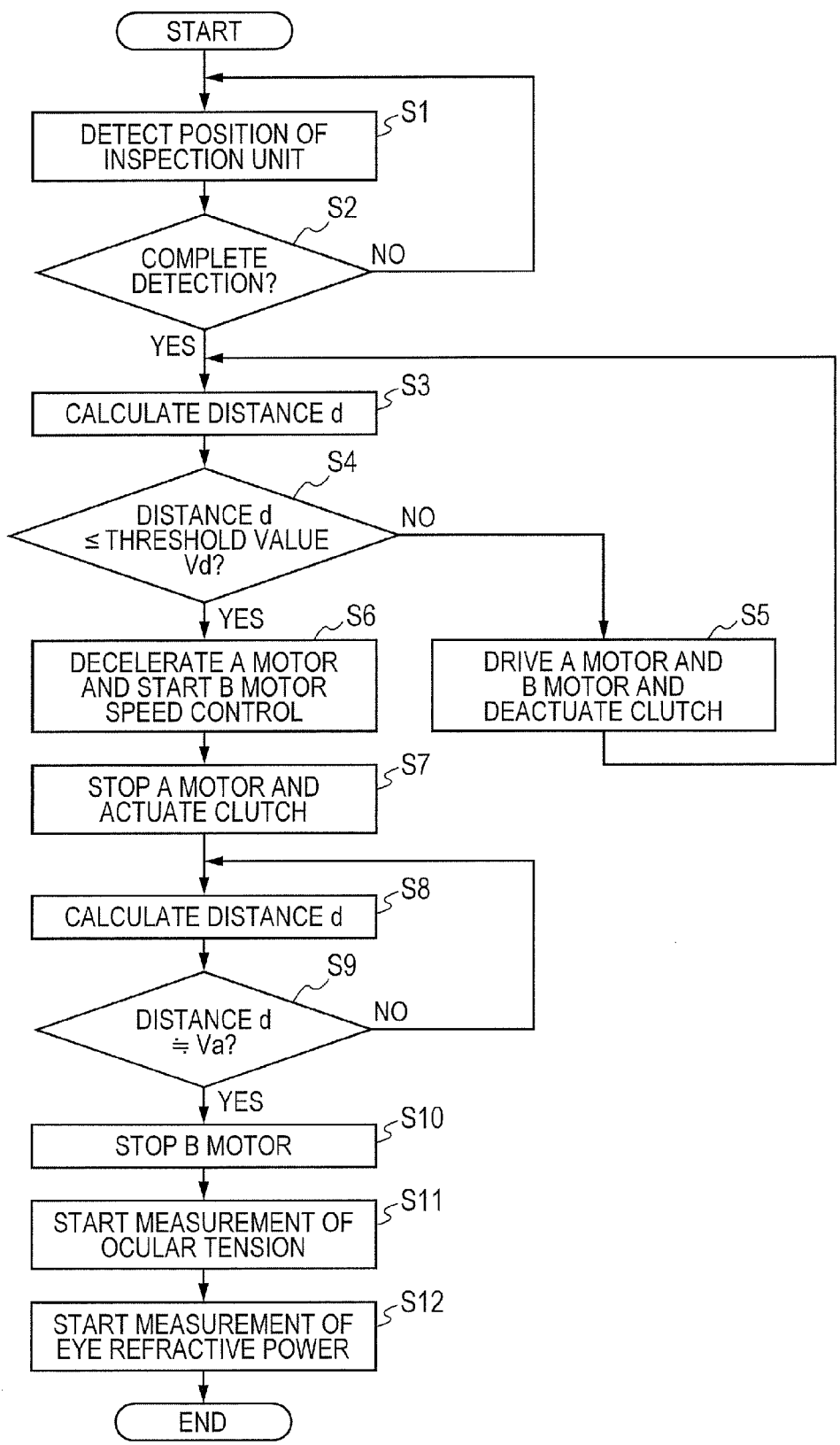
FIG. 7 is a flow chart illustrating steps of measuring an ocular tension and eye refractive power after performing a drive switch by the ophthalmologic apparatus according to the first embodiment.

A flow of switching between the first Z direction moving mechanism 1 and the second Z direction moving mechanism 2 is described following a flow of performing the measurement of the ocular tension and then measuring the eye refractive power in an actual eye inspection. FIG. 7 is a flow chart on the flow.

When the inspector presses the button (inspection switch) 116 to start the eye inspection, the calculation portion 82 in the main control portion 80 detects the position of the inspection unit 106 with respect to the eye to be inspected (Step S1). The position of the inspection unit 106 with respect to the eye to be inspected is detected by irradiating the eye to be inspected with a beam from inside a main body and receiving the beam, which has been reflected by a cornea of the eye to be inspected, by the image pickup element 94 provided inside the main body, and based on a result of signal processing by the signal processor 81 and the like. Here, the components such as the inspection unit 106 and the calculation portion 82 for measuring a positional relationship between the eye to be inspected and the inspection unit 106 based on data obtained from the inspection unit 106 form a measurement unit in this embodiment.

Whether or not the position of the inspection unit 106 has been detected is checked in Step S2. In a case where the determination portion 83 has determined that the beam reflected by the cornea of the eye to be inspected cannot be received by an image pickup portion and that the position of the inspection unit 106 with respect to the subject cannot be determined, the inspector brings the inspection unit 106 closer to a position at which the beam can be received and then the measurement is started again.

When the beam reflected by the cornea of the eye to be inspected can be received by the image pickup portion and the position of the inspection unit 106 with respect to the subject is detected, a distance d between the eye to be inspected and the inspection unit 106 is calculated in Step S3. Further, a comparison of the distance d and a threshold value Vd stored in the memory 95 is made in Step S4. The comparison step in Step S4 is executed by a component that functions as a determination unit for determining which of the measurement result of the measurement unit and the threshold value is large or small.

Figure 6:
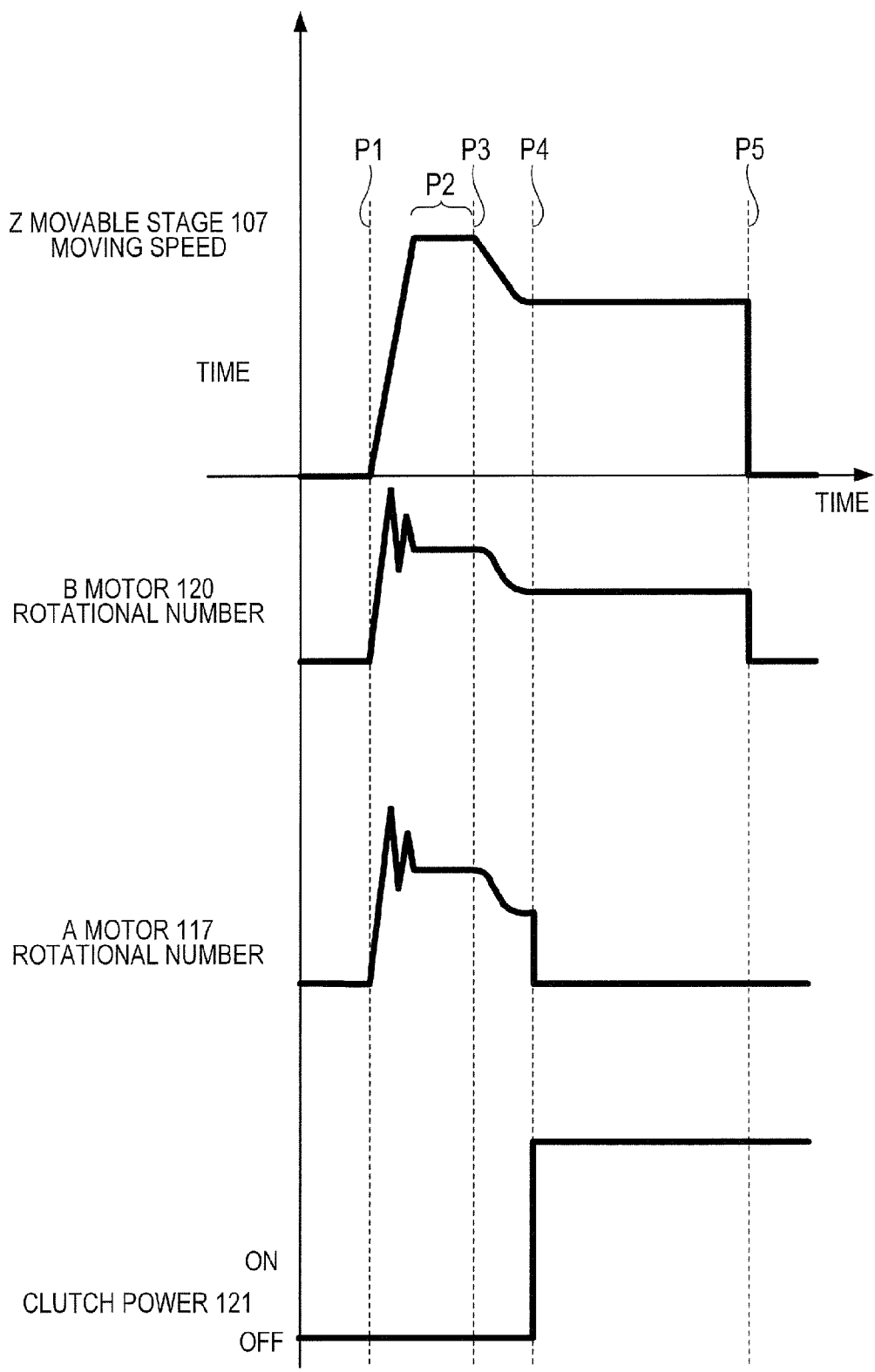
FIG. 6 is a graph showing a change in moving speed of the Z movable stage accompanying a clutch switch.

In a case where the distance d is larger than the threshold value Vd, which is stored in advance in the main body, and hence is not in a range that enables more precise alignment, the flow proceeds to Step S5. In Step S5, the Z direction A motor 117 provided in the first Z direction moving mechanism 1 and the Z direction B motor 120 provided in the second Z direction moving mechanism 2 are driven substantially at the same time (FIG. 6, P1). At that time, the actuation signal is not output from the main control portion 80 to the Z direction clutch 121, with the result that the rotation of the Z direction B motor 120 is not transmitted to the Z direction feed screw 122 and the Z direction B motor 120 rotates at idle. Moreover, at this time, a rotational number of the Z direction A motor 117 is set to a rotational number with which it is possible to obtain a moving speed of the Z movable stage 107 that exceeds a moving speed obtained when the second Z direction moving mechanism 2, which uses the Z direction feed screw 122, is used to drive the Z movable stage 107 at a maximum rotational number of the Z direction B motor 120. The maximum rotational number of the Z direction B motor 120 is generally determined by a relationship of motor specifications such as allowable torque and a load such as the feed screw, and the like.

During the alignment of the inspection unit 106, the position of the inspection unit 106 with respect to the eye to be inspected is detected. For this purpose, the beam reflected by the cornea of the eye to be inspected is received by the image pickup element 94 provided inside the main body, and the calculation of the distance d between the eye to be inspected and the inspection unit 106 and the comparison of the recalculated distance d and the threshold value Vd are performed again (Steps S3 and S4). In the case where the distance d is still larger than the threshold value Vd, the flow repeatedly transitions back to Step S5. Therefore, the Z direction A motor 117 is continuously driven, and the actuation signal is not output to the Z direction clutch 121. Therefore, the Z movable stage 107 is continuously moved by the first Z direction moving mechanism 1, which uses the rack and pinion drive (FIG. 6, P2).

In Step S4, in a case where it is determined that the distance d between the eye to be inspected and the inspection unit 106 is equal to or smaller than the threshold value Vd described above, the flow proceeds to Step S6. In Step S6, the main control portion 80 issues an instruction to reduce the rotational number of the Z direction A motor 117 (FIG. 6, P3). In other words, the main control portion 80 as a control unit switches, in the case where it is determined that the distance d between the eye to be inspected and the inspection unit 106 is the threshold value Vd or lower, the above-mentioned transmission of a driving amount from the first transmission to the second transmission. Note that, the determination is executed by a module in the main control portion 80, which functions as the determination unit for determining whether or not the distance between the eye to be inspected and the inspection unit 106 is the threshold value or less.

At that time, a driving rotational number of the Z direction A motor 117 is set to the rotational number that is smaller than the maximum rotational number with which the Z direction B motor 120 provided in the second Z direction moving mechanism 2, which uses the Z direction feed screw 122, can move the Z movable stage 107. Substantially at the same time, the main control portion sets the rotational number of the Z direction B motor 120 so that the moving speed of the Z movable stage 107 by the second Z direction moving mechanism 2 becomes substantially the same speed as the moving speed of the Z movable stage 107 by the first Z direction moving mechanism 1, and outputs a drive signal.

When it is determined that the rotational number of the Z direction B motor 120 has reached a set rotational number and the rotation has stabilized, the main control portion 80 outputs the actuation signal for operating the Z direction clutch 121. Substantially at the same time, the main control portion 80 outputs a stop signal to the Z direction A motor 117 (Step S7, FIG. 6, P4). This switches the drive for moving the Z movable stage 107 from the first Z direction moving mechanism 1 including the Z direction A motor 117 to the second Z direction moving mechanism 2 including the Z direction B motor 120.

According to this embodiment, the Z direction clutch 121 is used to switch the drive, with the result that the drive may be switched at substantially the same rotation and a shock at the time of switching may be reduced. Moreover, the switch is made from the rack and pinion drive to the feed screw drive to enable more precise alignment. Moreover, in this embodiment, the Z direction A motor and the Z direction B motor are driven substantially at the same time, and in the case where it is determined that the distance d is the threshold value Vd or less, the Z direction A motor is controlled to reduce the force for driving the first drive unit, and then the control is performed to switch from the first transmission of the driving force by the Z direction A motor to the second transmission by the Z direction B motor.

In other words, in this embodiment, both the motors are driven at the same time to realize the transmission switch that is operationally smooth. In this manner, the following effect is obtained: the actual moving state of the inspection unit 106 is adapted to the feeling received by the inspector when manually operating the joystick 101 to move the position of the inspection unit 106, with the result that a sense of discomfort is eliminated.

Thereafter, the calculation of the distance d and the comparison with an appropriate distance (focus position) Va in the inspection are further performed to continue the alignment (Steps S8 and S9). When it is determined in Step S9 that the position of the inspection unit 106 with respect to the eye to be inspected is at a correct position, a stop signal for the Z direction B motor 120 is output from the main control portion 80 (Step S10, FIG. 6, P5). This stops the rotation of the Z direction B motor 120 to enable the measurement of the ocular tension by the inspection unit 106. Thereafter in Step S11, the measurement of the ocular tension is performed, and measurement values corresponding to preset items are calculated and results thereof are displayed on the monitor 127 to complete the measurement of the ocular tension. Next in Step S12, the measurement of the eye refractive power is performed, and measurement values corresponding to preset items are calculated and results thereof are displayed on a display portion to complete the inspection of one eye.

Note that, in this embodiment, a timing at which the Z direction B motor 120 is rotated is before the measurement of the ocular tension. However, during the measurement of the ocular tension or during the measurement of the eye refractive power, the beam reflected by the cornea of the eye to be inspected may be received by the image pickup portion to detect the position of the inspection unit 106 with respect to the eye to be inspected as necessary, and in a case where the position is displaced, the Z direction B motor 120 may be rotated by a necessary amount to perform the alignment.

Next, in order to inspect the other eye, an operation of switching between the left and right eyes is performed.

Figure 8:
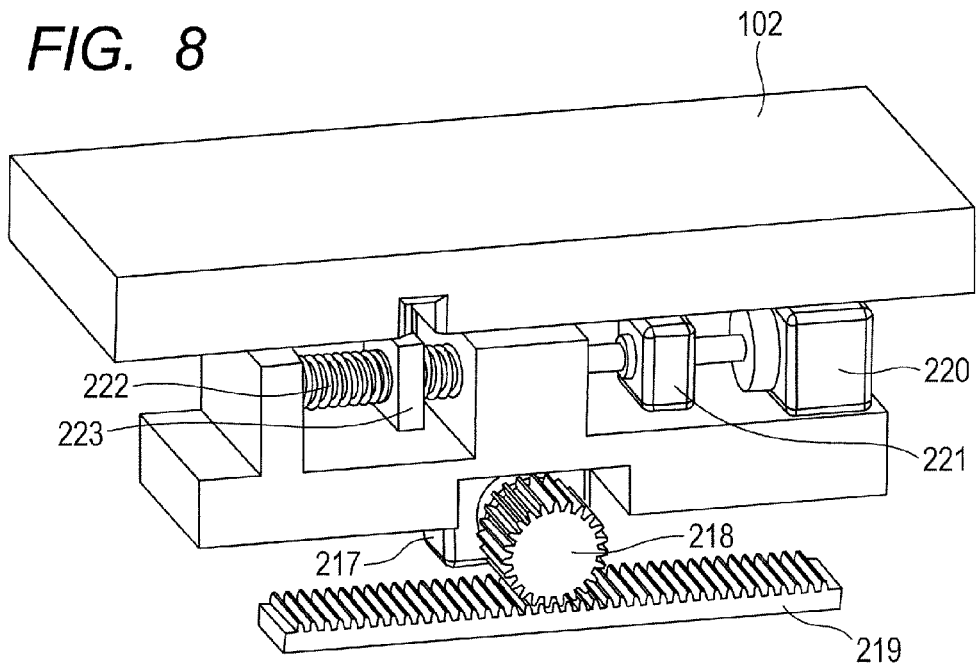
FIG. 8 is a view illustrating an overall structure of an X direction moving mechanism in the ophthalmologic apparatus illustrated in FIGS. 1A and 1B.

FIG. 8 is referenced to describe a configuration of the X movable stage drive unit 96. Note that, as with the Z movable stage drive unit 98 described above, the X movable stage drive unit 96 also includes an X direction A motor 217 provided in a first X direction moving mechanism and an X direction B motor 220 provided in a second X direction moving mechanism. Therefore, a detailed description of the corresponding components such as an X direction pinion 218, a rack 219, an X direction clutch 221, an X direction feed screw 222, and an X direction nut 223 is omitted, and a switching operation by those components is described. First, at the start of the switching between the left and right eyes, the inspection unit 106 exists at a position that significantly deviates from a threshold value in the X direction. Therefore, the X direction A motor 217 and the X direction B motor 220 are driven substantially at the same time as in the case where it is determined that the distance has exceeded the threshold value in Step S4 in the case of the Z movable stage described above. Moreover, an actuation signal from the main control portion 80 to the X direction clutch 221 is not output, with the result that rotation of the X direction B motor 220 is not transmitted to the X direction feed screw 222 and the X direction B motor 220 rotates at idle.

Here also, a rotational number of the X direction A motor 217 is set to a rotational number with which it is possible to obtain a moving speed of the X movable stage 102 that exceeds a moving speed obtained when the second X direction moving mechanism, which uses the X direction feed screw 222, is used to drive the X movable stage 102 at a maximum rotational number of the X direction B motor 220. The maximum rotational number of the X direction B motor 220 is generally determined by a relationship between motor specifications such as allowable torque and a load such as the feed screw, and the like.

During the switch between the left and right eyes, the X direction A motor 217 is rotated in response to a drive signal from the main control portion 80, but as with the driving in the Z direction, the X movable stage 102 is moved as necessary while detecting the position of the inspection unit 106 with respect to the eye to be inspected.

Moreover, in the above-mentioned operation, at the time of the switch between the left and right eyes, in a case of switching from one to the other of the left and right eyes, a determination as to whether or not a distance between the other eye and the inspection unit 106 is the threshold value or less is executed by the determination unit in the main control portion 80. Meanwhile, in the case where it is determined that the distance is the threshold value or less, the main control portion 80 controls the X direction clutch 221 to switch from a first transmission using a driving force from the X direction A motor 217 to a second transmission using a driving force from the X direction B motor 220.

Note that, in this embodiment, during the driving in the X direction, the inspection unit 106 is moved while detecting the position in the Z direction of the inspection unit 106 with respect to the eye to be inspected, but the X movable stage 102 may be moved while moving the Z movable stage 107 by an amount stored in advance in the main body.

When the movement of the inspection unit 106 in the X direction is complete, a comparison between the position of the inspection unit 106 and the threshold value stored in advance in the main body is made as described above. Based on a result of the comparison, as in the case of moving the Z movable stage 107, the X direction B motor 220, the X direction A motor 217, and the X direction clutch 221 are operated. Thereafter, as described above, the alignment of the inspection unit 106 is completed, and the measurement of the ocular tension and the measurement of the eye refractive power are performed to complete the inspection.

Note that, in this description, the measurement of the eye refractive power is performed after the measurement of the ocular tension is performed, but a case where the measurement of the eye refractive power is performed first or a case where only the measurement of the eye refractive power is performed may also be conceivable. In this case, the position of the inspection unit 106 with respect to the eye to be inspected, which is stored in advance in the main body, may be set to a position that is farther than that in the case where the measurement of the ocular tension is performed. In general, in the measurement of the ocular tension, the position of the inspection unit 106 with respect to the eye to be inspected is closer than that during the measurement of the eye refractive power, and the subject may feel pressure in some cases. Further, when the inspection unit 106 approaches the eye to be inspected at high speed by the first Z direction moving mechanism 1, the subject may sometimes feel more pressure. However, as in this embodiment, with the switch being made from the high-speed drive by the first Z direction moving mechanism 1 to the medium-speed drive by the second Z direction moving mechanism 2 at a position away from the eye to be inspected, it is possible to avoid the subject from feeling pressure and the like.

Moreover, in this embodiment, the rack and pinion is used as the first Z direction moving mechanism 1, and the feed screw drive is used as the second Z direction moving mechanism 2. The rack and pinion is often used in a case of converting a rotational motion into a linear motion, and has advantages in that it is possible to lengthen a movement stroke easily by increasing a length of the rack and in that production is also easy. However, a moving mechanism such as a belt drive may be used as a similar moving mechanism. On the other hand, the feed screw, which is used as the second Z direction moving mechanism 2, is used in the case of converting the rotational motion into the linear motion, and is often used in a case where highly precise alignment is required. However, while the feed screw has an advantage of enabling the high-precision alignment, high processing precision is required to process the feed screw, and hence when the length of the feed screw is increased, the cost is increased. Further, when the feed screw is lengthened, the high-precision processing becomes difficult, and hence it is not easy to lengthen the feed screw to lengthen the movement stroke. Therefore, when a configuration in which, as in this embodiment, the feed screw is used for the movement only in a range in which the high-precision alignment is required and the rack and pinion is used for the movement in a range in which the high-precision alignment is not required is adopted, it becomes easy to lengthen the movement stroke of a measurement portion. Moreover, a ball screw and other such alternative units may be used as the second Z direction moving mechanism 2.

Moreover, in this embodiment, the configuration in which the first drive unit and the second drive unit are different is described, but a configuration in which the first drive unit and the second drive unit have the same mechanism may be adopted. In this case, for example, pitches of feed screws or pitches of rack and pinions may be switched to change stopping accuracies in the drive units.

Note that, the above description on the Z movable stage drive unit 98 also applies to the X movable stage drive unit 96 having the similar configuration.

In this embodiment, the effect of reducing inspection time has been described, but when the drive to the first Z direction moving mechanism 1 and the like is interrupted, manual operation is also enabled. Therefore, it is also possible to obtain an effect that switching between an automatic electric inspection and a manual inspection is enabled as necessary to improve operability.

[Modified Example]

In the first embodiment described above, each of the first Z direction moving mechanism 1 and the second Z direction moving mechanism 2 includes a motor, but the present invention may be realized by using only one motor as a driving force for both the drive units. Such embodiment is described as a modified example below.

Note that, the functional components other than the moving mechanisms are the same as those described in the first embodiment of the present invention, and hence a description thereof is omitted here.

Figure 9:
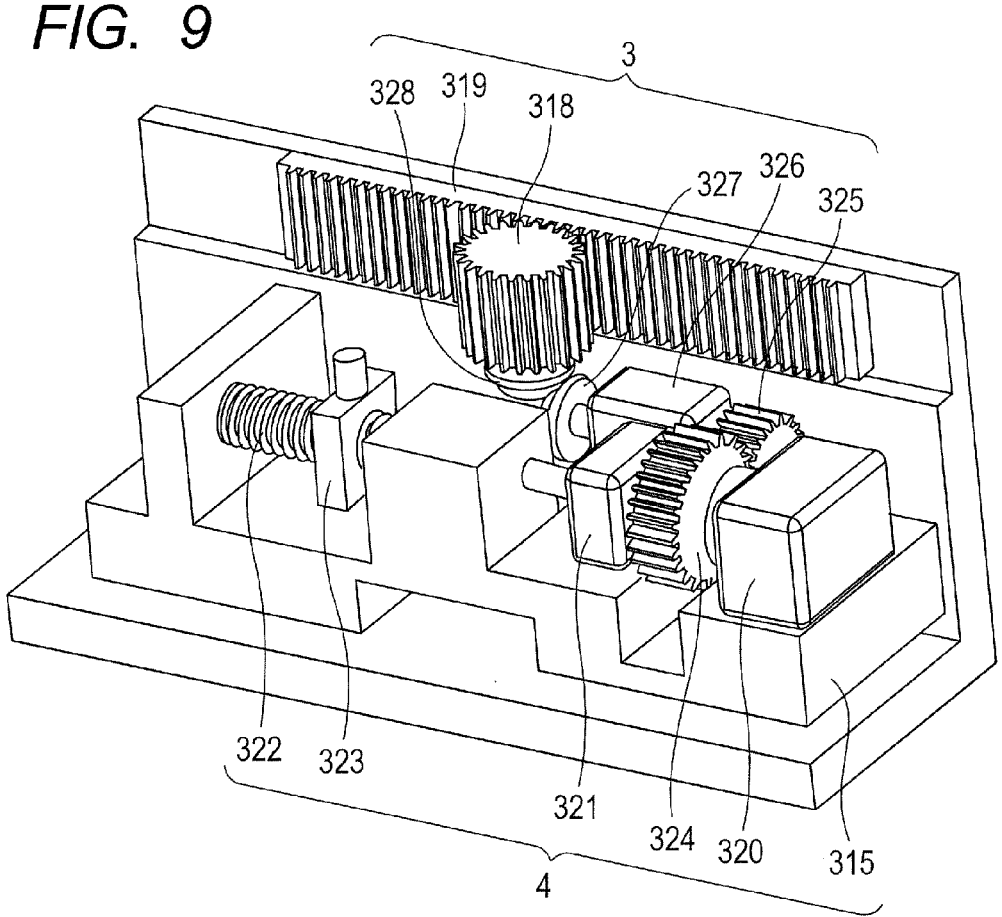
FIG. 9 is a view illustrating an overall structure of a Z direction moving mechanism according to a modified example of the present invention.

FIG. 9 is a view illustrating an overall structure of a first Z direction moving mechanism 3 as the first drive unit, a second Z direction moving mechanism 4 as the second drive unit, and a switching unit, which form the Z movable stage drive unit.

Figure 10:
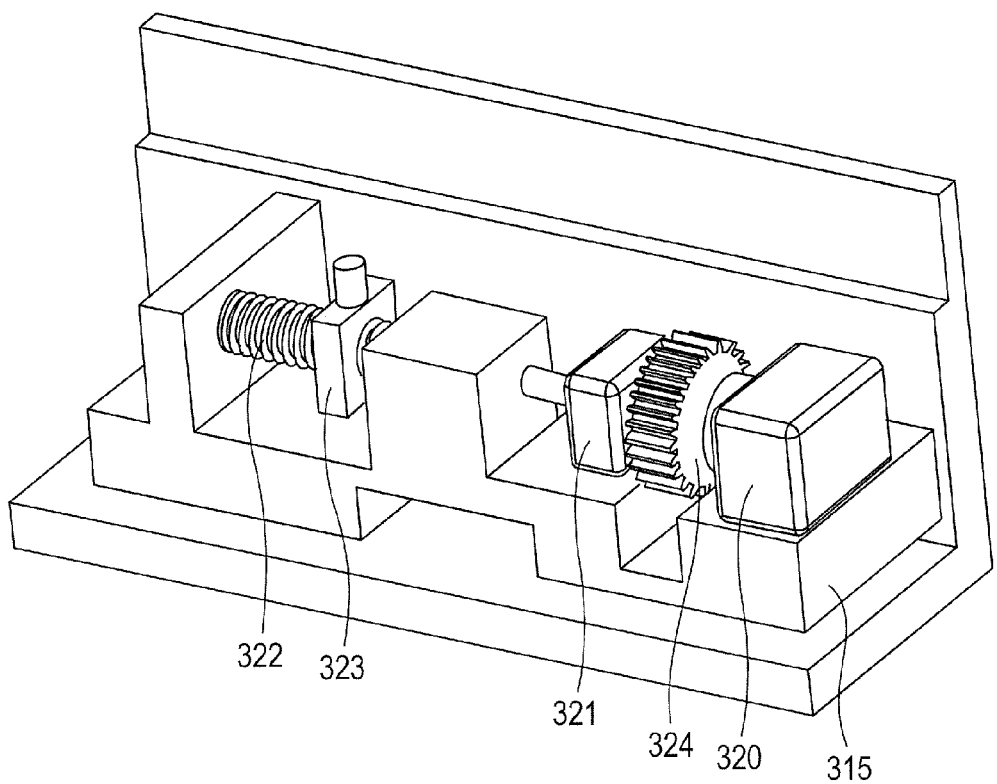
FIG. 10 is a view illustrating a first Z direction moving mechanism (1) in the modified example.

As illustrated in FIG. 10, the second Z direction moving mechanism 4 includes a Z direction motor 320, an A gear 324 as a drive transmission unit, a Z direction clutch 321 as the switching unit, and a Z direction feed screw 322. The Z direction feed screw 322 includes a Z direction nut 323. The Z direction feed screw 322 is held by a holding portion provided in a Z movable substage 315. The Z direction clutch 321 is provided between the Z direction motor 320 and the Z direction feed screw 322, and transmits rotation of the Z direction motor 320 to the Z direction feed screw 322 as necessary in response to an actuation signal from the main control portion 80. The A gear 324 has a function of distributing the rotation of the Z direction motor 320 to the first Z direction moving mechanism 3.

Figure 11:
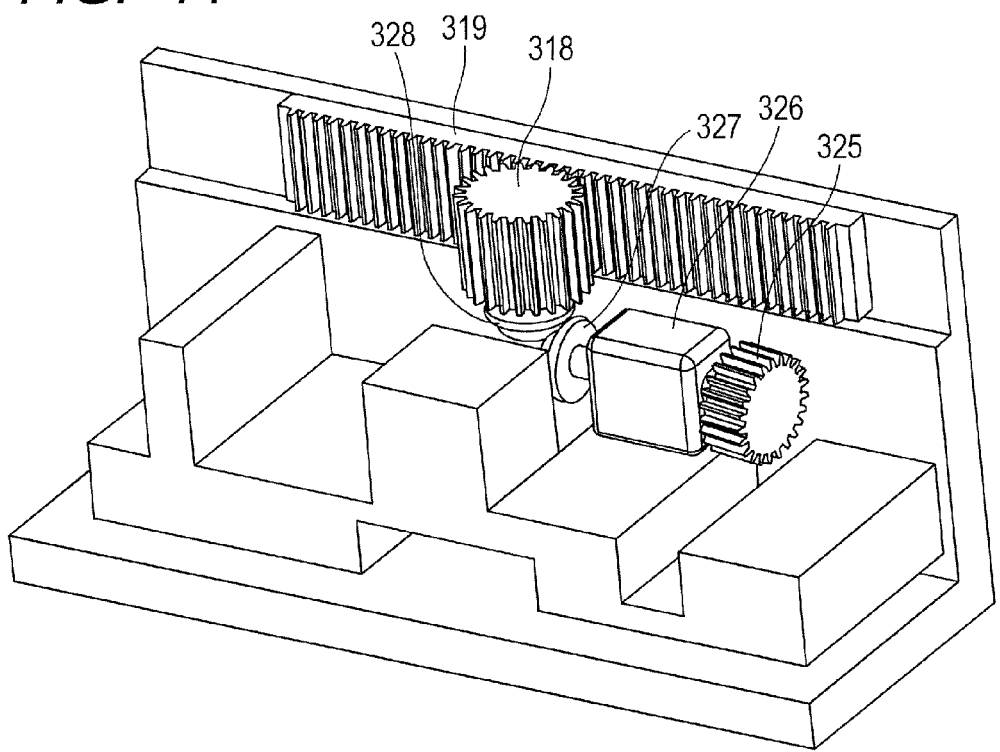
FIG. 11 is a view illustrating a second Z direction moving mechanism (2) in the modified example.

As illustrated in FIG. 11, as the first Z direction moving mechanism 3, a B gear 325 for receiving the drive transmitted from the second Z direction moving mechanism 4, a Z direction transmission 326 including a clutch function, a Z direction rack 319, and a Z direction pinion 318 are provided in the Z movable substage 315. In order to transmit the drive from the Z direction transmission 326 to the Z direction pinion 318, an A bevel gear 327 and a B bevel gear 328 are provided. The B bevel gear 328 is engaged with the Z direction pinion 318, and when the B bevel gear 328 rotates, the Z direction pinion 318 also rotates. The bevel gears are used in this embodiment, but other drive transmission units may be used instead.

When the drive is input to the first Z direction moving mechanism 3 by the B gear 325, the Z direction transmission 326 transmits and interrupts the drive in response to a signal output from the main control portion (not shown). When the drive is to be transmitted, an arbitrary gear ratio may be selected depending on the signal output from the main control portion 80, and hence an arbitrary rotational number may be selected for the Z direction pinion 318, with the result that the moving speed by the rack and pinion may also be arbitrarily selected.

The Z direction transmission 326 is a mechanism element for converting an input driving rotational number into an arbitrary driving rotational number steplessly, and although a stepless transmission using a transmission drive unit such as a belt is generally known, a transmission of another system may also be used.

(Flow of Switching the Drive)

Figure 12:
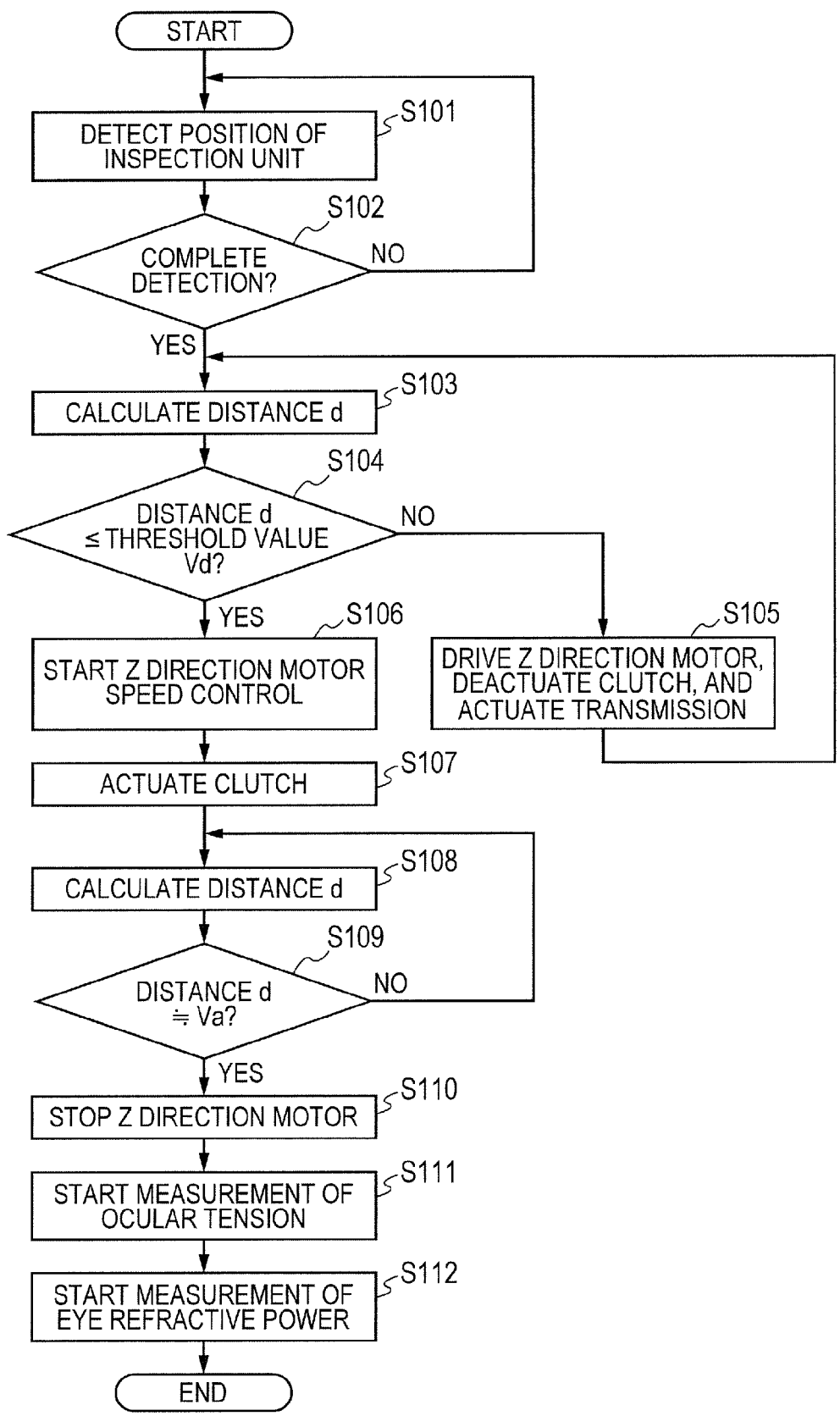
FIG. 12 is a flow chart illustrating steps of measuring an ocular tension and eye refractive power after performing a drive switch by an ophthalmologic apparatus according to the modified example.

A flow of switching between the first Z direction moving mechanism 3 and the second Z direction moving mechanism 4 is described following a flow of performing the measurement of the ocular tension and then measuring the eye refractive power in an actual eye inspection. FIG. 12 is a flow chart on the flow.

When the eye inspection is started, the calculation portion 82 in the main control portion 80 detects the position of the inspection unit 106 with respect to the eye to be inspected (Step S101). The position of the inspection unit 106 with respect to the eye to be inspected is detected by irradiating the eye to be inspected with a beam from inside the main body and receiving the beam, which has been reflected by the cornea of the eye to be inspected, by the image pickup element 94 provided inside the main body, and based on a result of signal processing by the signal processor 81 and the like.

Whether or not the position of the inspection unit 106 has been detected is checked in Step S102. In a case where the determination portion 83 has determined that the beam reflected by the cornea of the eye to be inspected cannot be received by an image pickup portion and that the position of the inspection unit 106 with respect to the subject cannot be determined, the inspector brings the inspection unit 106 closer to a position at which the beam can be received and then the measurement is started again.

When the beam reflected by the cornea of the eye to be inspected can be received by the image pickup portion and the position of the inspection unit 106 with respect to the subject is detected, the distance d between the eye to be inspected and the inspection unit 106 is calculated in Step S103. Subsequently, in Step S104, a comparison is made between the distance d and the threshold value Vd stored in advance in the memory 95. In a case where the distance d is larger than the threshold value Vd, the flow proceeds to Step S105 to drive the Z direction motor 320. At this time, the actuation signal is not output from the main control portion 80 to the Z direction clutch 321, and hence the rotation of the Z direction motor 320 is not transmitted to the Z direction feed screw 322. On the other hand, the driving force is transmitted to the Z direction transmission 326 via the A gear 324 and the B gear 325. At this time, the actuation signal is output from the main control portion 80 to the Z direction transmission 326, and hence the Z direction pinion 318 rotates so that the inspection unit 106 starts moving in the Z direction.

During the alignment of the inspection unit 106, the position of the inspection unit 106 with respect to the eye to be inspected is detected. For this purpose, the beam reflected by the cornea of the eye to be inspected is always received by the image pickup element 94 provided inside the main body, and the calculation of the distance d between the eye to be inspected and the inspection unit 106 and the comparison of the recalculated distance d and the threshold value Vd are performed again (Steps S103 and S104). In the case where the distance d is still larger than the threshold value Vd, the flow repeatedly transitions back to Step S105. Therefore, the Z direction motor 320 is continuously driven, and the actuation signal is not output to the Z direction clutch 321, with the result that a state in which the actuation signal is output to the Z direction transmission 326 is maintained. With this, the Z movable stage 107 is continuously moved by the first Z direction moving mechanism 3, which uses the rack and pinion drive.

In a case where it is determined that the distance d between the eye to be inspected and the inspection unit 106 is equal to or smaller than the threshold value Vd described above, the flow proceeds to Step S106. In Step S106, the main control portion 80 issues an instruction to reduce the rotational number of the Z direction motor 320. At this time, the Z direction transmission 326 is set so that the moving speed of the Z movable stage 107 by the first Z direction moving mechanism 3 and the moving speed of the Z movable stage 107 by the second Z direction moving mechanism 4 become substantially the same speed.

When it is determined that the rotational number of the Z direction motor 320 has reached a set rotational number and the rotation has stabilized, the main control portion 80 outputs the signal for operating the Z direction clutch 321 (Step S107). Substantially at the same time, an interruption signal is output to the Z direction transmission 326. This switches the drive for moving the Z movable stage 107 from the first Z direction moving mechanism 3 to the second Z direction moving mechanism 4.

According to this embodiment, the Z direction clutch 321 and the Z direction transmission 326 are used in combination to switch the drive, with the result that the drive may be switched at substantially the same rotation and a shock at the time of switching may be reduced.

Thereafter, the calculation of the distance d and the comparison with the appropriate distance (focus position) Va in the inspection are further performed to continue the alignment (Steps S108 and S109). When it is determined in Step S109 that the position of the inspection unit 106 with respect to the eye to be inspected is at a correct position, the stop signal for the Z direction motor 320 is output from the main control portion 80 (Step S110). This stops the rotation of the Z direction motor 320. Thereafter, in Step S111, the measurement of the ocular tension is performed, and measurement values corresponding to preset items are calculated and results thereof are displayed on the display portion to complete the measurement of the ocular tension. Next, in Step S112, the measurement of the eye refractive power is performed, and measurement values corresponding to preset items are calculated and results thereof are displayed on the display portion to complete the inspection of one eye.

Note that, in this embodiment, a timing at which the Z direction motor 320 is rotated is before the measurement of the ocular tension. However, during the measurement of the ocular tension or during the measurement of the eye refractive power, the beam reflected by the cornea of the eye to be inspected may be received by the image pickup portion to detect the position of the inspection unit 106 with respect to the eye to be inspected as necessary, and in a case where the position is displaced, the Z direction motor 320 may be rotated by a necessary amount to perform the alignment. The inspection of one eye is completed in this manner.

Next, in order to inspect the other eye, an operation of switching between the left and right eyes is performed. Here, in the flow of the drive switch described in the first embodiment, the X movable stage drive unit and the Z movable stage drive unit have the same configuration as described above. The same applies to this embodiment, and also in the X movable stage drive unit, the motor generating the driving force for the feed screw and the motor generating the driving force for the rack and pinion are integrated. Further, the X movable stage drive unit is similar to the Z movable stage drive unit in terms of the drive switch described above in that a gear for distributing the drive is added to the drive unit using the feed screw, and in that a gear for transmitting the drive and a decelerator are used for the drive unit using the rack and pinion. Therefore, a duplicate detailed description thereof is omitted here.

For the reduction in alignment time, as described above, it is effective to change a drive speed in the up and down drive and the like of the inspection unit. However, in the actual inspection time of the eye to be inspected, there are cases where the changing time in the left and right eye inspection is longer than the alignment time. Moreover, in order to reduce the changing time in the right and left eye inspection, it is possible to increase a motor rotational speed during the changing. However, as in the feed screw drive, for example, in a case where the load torque for driving is large, there is a need to use a motor having large allowable torque in order to reduce the changing time by the motor rotational number. Therefore, in reality, due to the constraints of cost and space, there are cases where such motor is difficult to adopt.

As described above, in the case where it is preferred to drive the inspection unit at a high drive speed, the rack and pinion system, which is inferior in stopping accuracy but is advantageous in terms of speed, is adopted. Moreover, in the case where the stopping accuracy is important, the feed screw system, which is preferred in terms of the stopping accuracy but is inferior in drive speed, is adopted. Then, both of the systems are combined to keep the time required for the alignment short and enable the increase in stopping accuracy. The combination also has an advantage in terms of the required torque of the motor described above at the same time, that is, the drive torque of the driving motor of the feed screw is small, which allows its use even when the drive speed is relatively low. Therefore, in the case where the position of the inspection unit with respect to the eye to be inspected is far, it is possible to suitably change the moving speed of the inspection unit, and to reduce the inspection time.

[Other Embodiments]

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-056456, filed Mar. 19, 2014, which is hereby incorporated by reference wherein in its entirety.

What is claimed is:

1. An ophthalmologic apparatus comprising:
   an eye inspection unit configured to inspect an eye of a subject;
   a first moving mechanism configured to move the eye inspection unit in a predetermined direction;
   a first motor configured to drive the first moving mechanism;
   a second moving mechanism configured to move the eye inspection unit in the predetermined direction and to have stopping accuracy that is higher than stopping accuracy of the first moving mechanism;
   a second motor which is different from the first motor and which is configured to drive the second moving mechanism; and
   a switching unit configured to switch between the movement by the first moving mechanism and the movement by the second moving mechanism.

2. An ophthalmologic apparatus according to claim 1, further comprising a measurement unit configured to measure a positional relationship between the eye and the eye inspection unit,
   wherein the switching unit switches between the movement by the first moving mechanism and the movement by the second moving mechanism depending on a measurement result of the measurement unit.

3. An ophthalmologic apparatus according to claim 2, further comprising a determination unit configured to determine which of the measurement result of the measurement unit and a threshold value is large or small,
   wherein the switching unit switches, in a case where it is determined that the measurement result is smaller than the threshold value, between the movement by the first moving mechanism and the movement by the second moving mechanism.

4. An ophthalmologic apparatus according to claim 3, wherein in a case where the eye inspection unit is moved in a front and back direction when viewed from the subject, and in the case where it is determined that the measurement result is smaller than the threshold value, the switching unit executes a switch from the movement by the first moving mechanism to the movement by the second moving mechanism.

5. An ophthalmologic apparatus according to claim 1, wherein the switching unit drives both the first moving mechanism and the second moving mechanism, and in a case where a moving speed of the eye inspection unit by the first moving mechanism and a moving speed of the eye inspection unit by the second moving mechanism become substantially the same speed, executes a switch from the movement by the first moving mechanism to the movement by the second moving mechanism.

6. An ophthalmologic apparatus according to claim 1, wherein the first moving mechanism comprises a rack and pinion, and
wherein the second moving mechanism comprises a feed screw.

7. An ophthalmologic apparatus according to claim 1, wherein the switching unit comprises a clutch.

8. An ophthalmologic apparatus according to claim 1, wherein the first motor and the second motor start driving substantially at the same time, and
wherein in a case where it is determined that a distance between the eye and the eye inspection unit is a threshold value or less, (1) the first motor is controlled to reduce a force with which the first motor drives the first moving mechanism, and (2) the switching unit switches from a first transmission by the first motor to a second transmission by the second motor.

9. A method of controlling an ophthalmologic apparatus including (1) an eye inspection unit configured to inspect an eye of a subject, (2) a first moving mechanism configured to move the eye inspection unit in a predetermined direction, (3) a first motor configured to drive the first moving mechanism, (4) a second moving mechanism configured to move the eye inspection unit in the predetermined direction and to have stopping accuracy that is higher than stopping accuracy of the first moving mechanism, and (5) a second motor which is different from the first motor and which is configured to drive the second moving mechanism, the method comprising a step of:
switching between the movement by the first moving mechanism and the movement by the second moving mechanism.

10. A non-transitory computer-readable medium having recorded thereon a program for causing a computer to execute the method of controlling an ophthalmologic apparatus of claim 9.

11. An ophthalmologic apparatus comprising:
an eye inspection unit configured to inspect an eye of a subject;
a first moving mechanism configured to move the eye inspection unit in a predetermined direction;
a second moving mechanism configured to move the eye inspection unit in the predetermined direction and to have stopping accuracy that is higher than stopping accuracy of the first moving mechanism;
a driving source configured to provide a force which is transmitted to the first moving mechanism for driving the first moving mechanism through a first transmission unit, and which is transmitted to the second moving mechanism for driving the second moving mechanism through a second transmission unit; and
a switching unit configured to switch between use of the first transmission unit for transmitting the force to the first moving mechanism and use of the second transmission unit for transmitting the force to the second moving mechanism.

12. An ophthalmologic apparatus according to claim 11, further comprising:
a determination unit configured to determine whether or not a distance between the eye and the eye inspection unit is a threshold value or less; and
a control unit configured to control, in a case where it is determined that the distance is the threshold value or less, the switching unit to switch from the first transmission unit to the second transmission unit.

13. An ophthalmologic apparatus according to claim 11, further comprising:
a determination unit configured to determine, in a case of switching from one to another one of right and left eyes, whether or not a distance between the another one and the eye inspection unit is a threshold value or less; and
a control unit configured to control, in a case where it is determined that the distance is the threshold value or less, the switching unit to switch from the first transmission unit to the second transmission unit.

14. An ophthalmologic apparatus according to claim 11, wherein the first moving mechanism comprises a rack and pinion,
wherein the second moving mechanism comprises a feed screw, and
wherein the switching unit comprises a clutch.

15. An ophthalmologic apparatus according to claim 11, wherein the first transmission unit is a transmission having a clutch function,
wherein the second transmission unit is a clutch, and
wherein the switching unit switches from the use of the first transmission unit to the use of the second transmission unit, in a state that a first moving speed of the eye inspection unit moved by the first moving mechanism is set by the transmission of the first transmission unit to the same speed as a second moving speed of the eye inspection unit moved by the second moving mechanism.

16. A method of controlling an ophthalmologic apparatus including (1) an eye inspection unit configured to inspect an eye of a subject, (2) a first moving mechanism configured to move the eye inspection unit in a predetermined direction, (3) a second moving mechanism arranged to be able to move the eye inspection unit in the predetermined direction, and (4) a driving source configured to provide a force which is transmitted to the first moving mechanism for driving the first moving mechanism through a first transmission unit, and which is transmitted to the second moving mechanism for driving the second moving mechanism through a second transmission unit, the method comprising a step of:
switching between use of the first transmission unit for transmitting the force to the first moving mechanism, and use of the second transmission unit for transmitting the force to the second moving mechanism.

17. A non-transitory computer-readable medium having recorded thereon a program for causing a computer to execute the method of controlling an ophthalmologic apparatus of claim 16.

* * * * *